United States Patent
Metzger

(10) Patent No.: US 6,986,791 B1
(45) Date of Patent: Jan. 17, 2006

(54) KNEE PROSTHESIS WITH MOVEABLE POST

(75) Inventor: Robert Metzger, Walkarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 10/413,940

(22) Filed: Apr. 15, 2003

(51) Int. Cl.
    *A61F 2/38* (2006.01)

(52) U.S. Cl. .............. 623/20.24; 623/20.28; 623/20.29; 623/20.33

(58) Field of Classification Search ... 623/20.14–20.34
    See application file for complete search history.

(56) References Cited

U.S. PATENT DOCUMENTS

| | | | |
|---|---|---|---|
| 3,869,729 A * | 3/1975 | Attenborough | 623/20.25 |
| 4,224,697 A | 9/1980 | Murray et al. | |
| 4,790,853 A * | 12/1988 | Engelbrecht et al. | 623/20.25 |
| 4,950,297 A | 8/1990 | Elloy et al. | |
| 5,116,376 A | 5/1992 | May | |
| 5,139,521 A * | 8/1992 | Schelhas | 623/20.25 |
| 5,314,483 A * | 5/1994 | Wehrli et al. | 623/20.29 |
| 5,370,701 A * | 12/1994 | Finn | 623/20.25 |
| 5,702,466 A | 12/1997 | Pappas et al. | |
| 5,755,804 A * | 5/1998 | Schmotzer et al. | 623/20.24 |
| 5,824,102 A | 10/1998 | Buscayret | |
| 6,019,794 A * | 2/2000 | Walker | 623/20.22 |
| 6,039,764 A | 3/2000 | Pottenger et al. | |
| 6,080,195 A | 6/2000 | Colleran et al. | |
| 6,099,570 A | 8/2000 | Livet et al. | |
| 6,117,175 A | 9/2000 | Bosredon | |
| 6,210,444 B1 | 4/2001 | Webster et al. | |
| 6,210,445 B1 | 4/2001 | Zawadzki | |
| 6,217,618 B1 | 4/2001 | Hileman | |

* cited by examiner

*Primary Examiner*—David J. Isabella
(74) *Attorney, Agent, or Firm*—Harness, Dickey & Pierce, P.L.C.

(57) ABSTRACT

A knee prosthetic for implantation includes a mobile rotatable posterior stabilized (PS) post. The mobile PS post may rotate or distract superiorly relative to a tibial component. The mobile PS post may rotate with the femur after implantation, at least for a selected distance. Various exterior shapes of the mobile PS post and/or a bore formed in the tibial component may be selected to limit the amount of rotation. Various materials may be chosen to form the mobile PS post depending upon desired qualities.

15 Claims, 6 Drawing Sheets

KNEE PROSTHESIS WITH MOVEABLE POST

FIELD

The present invention relates to knee prosthetics, and more particularly to knee prosthetics having a rotating post extending from the tibial component.

BACKGROUND

The human anatomy includes many articulating portions. For example, the femur and tibia form the knee of the human anatomy and articulate to allow ease of walking and mobility. Nevertheless, over time, disease and injury may deteriorate the knee joint, such that articulation of the joint becomes painful or impractical. When such deformities or injuries occur, anatomical replacements, particularly implants and prosthetics, can be placed in the femur or the tibia, or both to replace the damaged portions and restore the natural articulation of the knee.

Due to injury or disease, however, replacing only the articulating portions is not always practical or possible. Particularly, if certain tissues such as ligaments, tendons, or muscle are not able to withstand natural anatomical strains, the knee prosthetic required may need to constrain or stabilize the knee. Specifically, ligaments, such as the anterior cruciate ligament or the posterior cruciate ligament, may no longer be able to withstand the natural stresses, due to walking or other activities, and may be compensated for with a prosthetic knee.

One exemplary component to replace such ligaments, or general weakening of the soft tissue, is a posterior stabilized knee prosthetic. For example, the posterior stabilized knee prosthetic may include a post, particularly a posterior stabilized (PS) post, which extends superiorly from a tibial component to operably engage a femoral component, or the femur, to constrain posterior movement of the knee, which is not otherwise able to be constrained by the remaining soft tissues. Generally, the PS post is a fixed portion of the tibial component and simply extends from the tibial component to operably engage a portion of the femur to constrain selected movement of the femur.

SUMMARY

A knee prosthetic for implantation in the anatomy that includes a mobile posterior stabilized (PS) post. The PS post may also include a selected amount of rotation in the transverse plane. Generally, this allows the knee prosthetic, and particularly the PS post, degrees of freedom not otherwise realized. In addition, including a mobile PS post can reduce the wear of the mobile PS post relative to a fixed post that articulates more forcefully with the femur or femoral component.

Examples include, a knee prosthetic, having a mobile PS post, and a fixed bearing. Therefore, while the PS post is able to rotate a selected amount, the bearing is fixed relative the tibial component. Another example includes a knee prosthetic having a mobile PS post, but otherwise a fully constrained knee prosthetic. This includes certain advantages of a mobile PS post, but allows for a maximum constraining of the knee. A further example includes a knee prosthetic having a mobile bearing, but including a tibial component operably associated with a PS post to allow a selected amount of medial lateral rotation. Any other appropriate type of knee may also incorporate these features.

A first embodiment includes a prosthetic for implantation to replace a portion of a knee joint. The prosthetic includes a tibial component. The tibial component has a tibial tray and a tibial stem that extends from the tibial tray. A bearing member operatively engages the tibial tray, and is fixed relative to the tibial tray. A constraining member extends from the tibial tray that may operably engage a femoral component. The constraining member is able to move a selected amount, after implantation of the prosthetic, relative to the tibial tray.

A second embodiment includes a prosthetic for implantation to replace a portion of the knee joint including a femoral component having a first condyle and a second condyle. The prosthetic further includes a tibial component having a tibial tray and a tibial stem that extends from the tibial tray. A bearing member operatively engages the tibial tray, including a first condyle bearing surface and a second condyle bearing surface. A constraining member is fixed relative to the tibial tray after the prosthetic is implanted. The constraining member is able to move a selected amount after implantation of the prosthetic relative to the tibial component.

A third embodiment includes a knee prosthetic for implantation into a boney structure including a tibial component having a tibial tray and a tibial stem extending from the tibial tray. The tibial stem operably engages the boney structure after implantation. A bearing component is provided that may articulate with the tibial tray. A constraining member having a first portion and a second portion, wherein the second portion engages a stem bore defined by the tibial stem. The stem bore limits rotation of the constraining member to about 180 degrees.

A fourth embodiment includes a prosthetic for implantation to replace a knee joint having a femoral component including a first condyle and a second condyle. An inter-condylar box is disposed between the first condyle and the second condyle. A tibial component has a tibial tray and a tibial stem that extends from the tibial tray to operably engage a tibia after implantation. A constraining member limits the motion of the prosthetic, in a first manner, after implantation. A post, to limit a motion of the prosthetic in a second manner, has a first portion and a second portion. The tibial component defines a stem bore to operably engage the second portion. The first portion operably engages the inter-condylar box to stabilize the knee joint after implantation of the prosthetic.

According to a fifth embodiment a method for replacing a natural joint includes implanting a prosthetic in a knee joint of an anatomy, including implanting a tibial component and a femoral component that are operable to articulate relative one another. The method comprises implanting the tibial component in the tibia and implanting the femoral component in the femur. A rotatable post is provided to articulate between the femoral component and the tibial component after implantation. Also, a rotational freedom for the rotatable post is selected.

Further areas of applicability will become apparent from the detailed description provided hereinafter. It should be understood that the detailed description and various examples, while indicating the various embodiment, are intended for purposes of illustration only and are not intended to limit the scope of the following claims.

BRIEF DESCRIPTION OF THE DRAWINGS

The present description will become more fully understood from the detailed description and the accompanying drawings, wherein.

DETAILED DESCRIPTION OF VARIOUS EMBODIMENTS

The following description of various embodiments is merely exemplary in nature and is in no way intended to limit the scope of the following claims, application, or uses. It will be understood that the following description may be used in any appropriate knee prosthesis. For example the rotatable post may be used in a cruciate retaining, a posterior stabilized, fully constrained, or hinged knee. Moreover, the rotatable post may be used with a fixed or mobile bearing knee.

Figure 1:
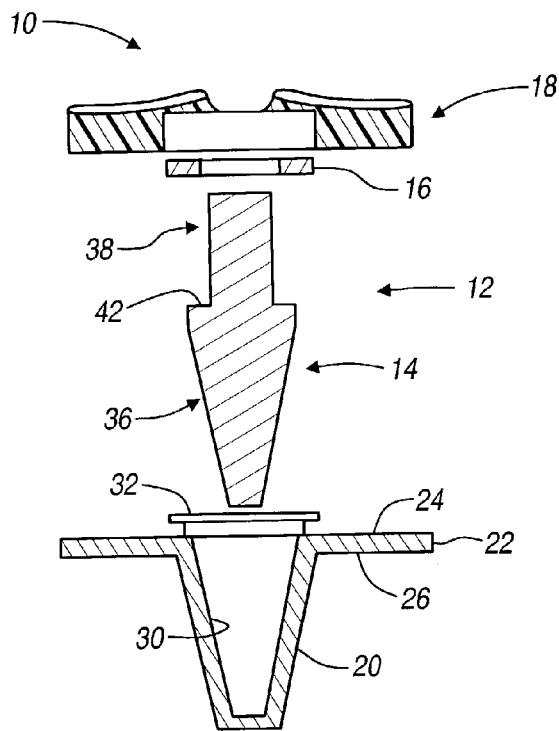
FIG. 1 is an exploded cross-sectional view of a tibial component according to a first embodiment.
Figure 2:
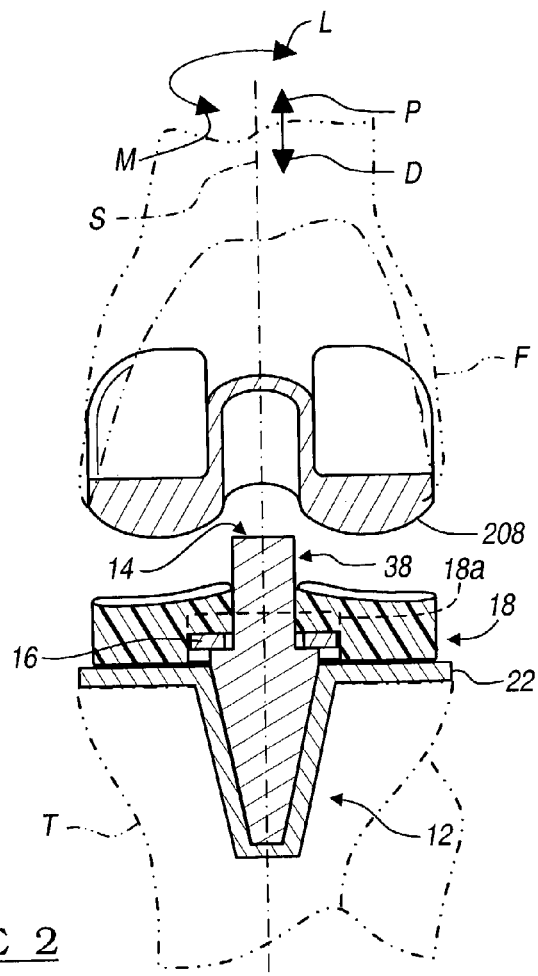
FIG. 2 is a cross-sectional view of an assembled tibial component illustrated in FIG. 1.
Figure 1A:
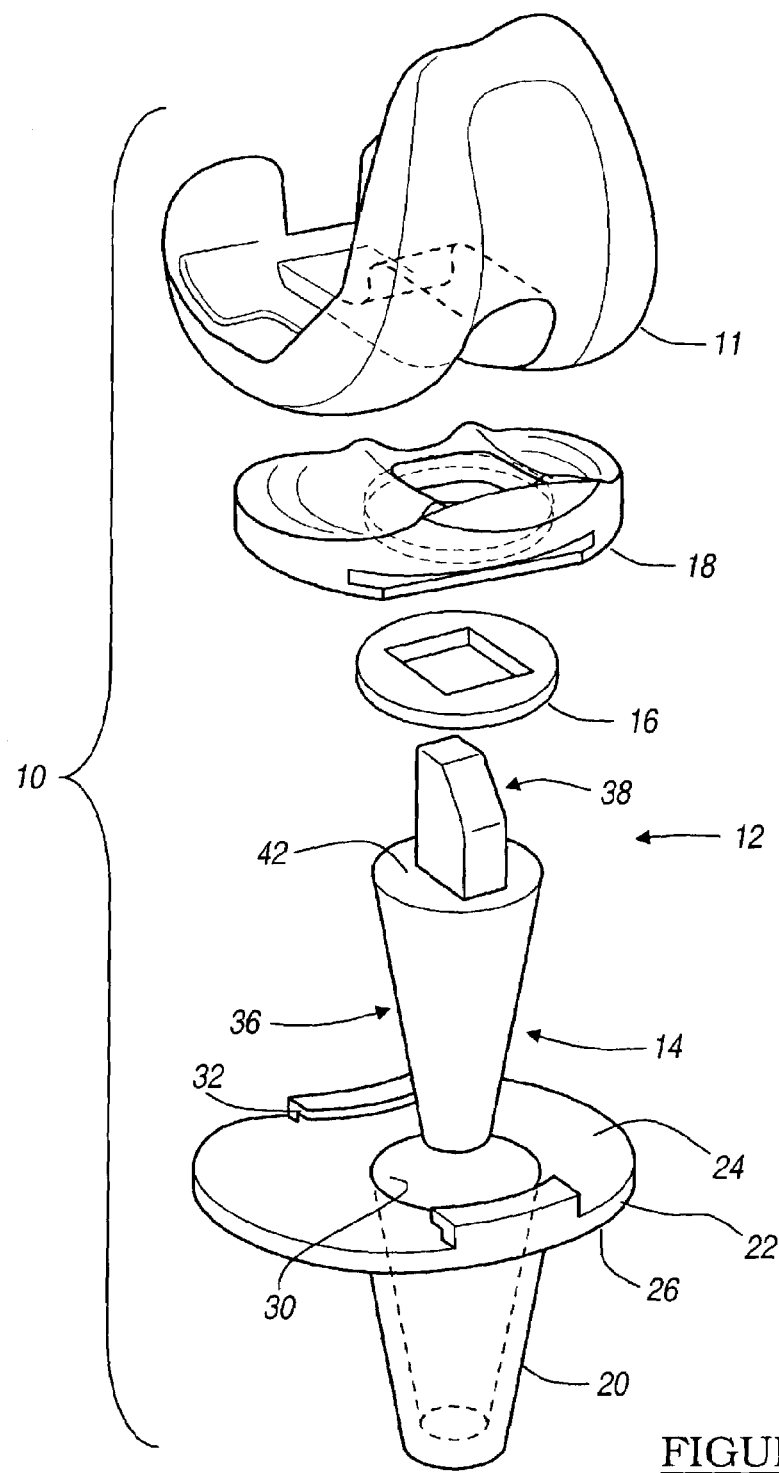
FIG. 1a is a perspective exploded view of the tibial component in FIG. 1.

With reference to FIGS. 1, 1a, and 2, a mobile post posterior stabilized (PS) knee prosthetic 10 includes femoral component 11, a tibial component 12, a mobile and/or rotatable PS post 14, a washer 16, and a bearing component 18. The rotatable PS post 14 constrains the varus/valgus motion of a femur (F) relative to a tibia (T) after implantation. As described more fully herein, the mobile PS post 14 may both rotate and distract relative to the tibial component 12. The tibial component 12 generally includes a tibial stem 20 that extends along a stem axis (S) and further able to extend into the tibia (T) for implantation. The tibial stem 20 may be formed in any appropriate manner, such as a square or as an I-beam to resist rotation after implantation.

Adjacent a superior portion of the tibial component 12 is a tibial tray 22. The tibial tray 22 rests upon the superior portion of the tibia after implantation. The tibial tray 22 may be polished to reduce the possibility of wear debris forming after implantation of the tibial component 12. When used with the fixed bearing 18, however, polishing the tibial tray 22 may not be necessary. An inferior side 26 of the tibial tray 22 may include regions, such as coatings for bone ingrowth or for cementation to the tibia.

Formed on the interior of the tibial stem 20 is a PS post articulating bore or stem bore 30. The PS post articulation bore 30 is adapted to rotatably receive a portion of the mobile PS post 14 during or after implantation of the tibial component 12. Particularly, and according to various embodiments, a first or inferior portion 36 of the PS post 14 articulates within the bore 30.

The rotatable PS post 14 is able to rotate medially in the direction of arrow M and laterally in the direction of arrow L. The medial and lateral rotation is around the longitudinal axis S of the stem 20. Therefore, the rotatable post 14 is able to move with the femur F after implantation of the prosthetic, as described more fully herein. In addition, the rotatable PS post 14 is able to move both proximally and in the direction of arrow P and distally in the direction of arrow D relative to the femur F. The movement proximally P and distally D is also along the axis S defined by the stem 20. Therefore, the mobile PS post 14 is able to rotate medially M and laterally L and move proximally P and distally D relative the stem 20. When moving proximally from the bore 30 the first portion 36 including a shoulder 42 of the mobile PS post 14 is able to move proximally P into the area shown in phantom 18a of the bearing 18. It will be understood, however, that the area 18a may not be present or may be varied in depth to select a proximal movement of the mobile PS post 14. It will also be understood that the post 14 may be fixed relative to superior and inferior articulation. Yet, while the femoral component rotates relative a fixed bearing, described herein, it could distract from the tibial component 12.

Formed on the tibial component 12 may be one or more bearing fixation or locking portions 32. The bearing locking portion 32 locks the bearing 18 in a fixed position relative to the tibial component 12, such that the bearing 18 is not able to move or articulate after implantation. This allows the retention of the bearing 18 in a selected position and a selected proximal movement of the post 14 by providing the area 18a if selected.

Any of the portions of the tibial component 12, including the PS post articulation bore 30 or the bearing locking portion 32, may be polished to provide for a substantial friction free interaction with other components. Alternatively, certain textures may be left on the component to provide a desired amount of friction or fixation. In addition, the tibial component 12 is generally formed of a metal or appropriate biocompatible materials. Examples include various stainless steels, titanium, or alloys of chromium, cobalt, and molybdenum. Generally, any appropriate biocompatible metal that has appropriate strength and wear qualities may be used for the tibial component 12.

The mobile PS post 14, according to this embodiment, is formed of a polymer material. For example, the mobile PS post 14 can be formed of an ultra high molecular weight polyethylene (UHMWPE). It will be understood that any appropriate polymer material may be used, which includes selected biocompatibility and strength characteristics. Although, as described herein, the mobile PS post may be modular thus including both metal and polymer portions.

The mobile PS post 14 may also be referred to as a constraining member or a stabilizing member. The mobile PS post 14 generally includes the inferior tibial component or first portion 36. The first portion 36 of the mobile PS post 14 includes a taper that is adapted to at least partially mate with the PS post articulating bore 30 formed in the tibial stem 20 of the tibial component 12. Although the first portion 36 defines a substantially complimentary shape to the mobile PS post articulating bore 30, it is generally smaller than the dimensions of the articulating bore 30. This allows the mobile PS post 14 to move or articulate within the articulating bore 30. Moreover, a locking fit is not created between the mobile PS post 14 and the tibial component 12 so that the mobile PS post 14 is able to move after implantation.

On a superior portion of the mobile PS post 14 is formed a second or post portion 38. The second portion 38 extends superiorly from the tibial component 12 after implantation of the mobile PS post 14. Therefore, the second portion 38 is able to extend to operably engage or articulate with the femur or the femoral component after implantation into the anatomy. Particularly, the second portion 38, is able to either or both rotate medial laterally after implantation or to distract superiorly. The operable engagement of the first portion 36 with the articulating bore 30 of the tibial component 12 allows the second portion 38 to move relative the tibial component 12 after implantation. As described in detail further herein, specific designs of the first portion 36 and/or the articulating bore 30 can be used to select the particular amount of medial-lateral rotation or superior distraction. Moreover, the dimensions of the second portion 38 may be selected in any appropriate manner to properly articulate with the selected femur or femoral component.

The transition shoulder 42 is formed between the first portion 36 and the second portion 38. The shoulder 42 allows the first portion 36 to be selected of a particular size to properly articulate in the articulating bore 30 and provide substantial strength to the mobile PS post 14. Moreover, the shoulder 42 allows the washer 16 to rest upon the mobile PS post 14. The washer 16 is formed of a metal, which may be the same metal as the tibial component 12, or any other appropriate biocompatible metal. The washer 16 allows for smooth articulation between the mobile PS post 14 and the bearing 18. Generally, the bearing 18 is formed of a material similar to the material of the mobile PS post 14. For example, the bearing 18 may be formed of a ultra-high molecular weight polyethylene, similar to the material of the mobile PS post 14.

With continuing reference to FIGS. 1 and 2, the tibial component 10 is assembled and implanted in the tibia (T). Similarly, a femoral component 11 is implanted in the femur (F). The femoral component 11 is described in detail herein. When assembled, the bearing 18 rests on the superior portion 24 of the tibial tray 22. Therefore, there is substantially no direct contact between the bearing 18 and the rotatable PS post 14. The washer 16 substantially eliminates poly-to-poly contact between the mobile PS post 14 and the bearing 18. Because the mobile PS post 14 is able to at least rotate medially-laterally, relative to the bearing 18, the washer 16 substantially reduces or eliminates poly-to-poly contact when the mobile PS post 14 and the bearing 18. This substantially reduces wear during articulation after implantation of the tibial component 10.

Although the first portion 36 of the rotating post 14 is illustrated to be substantially a taper or conical, it will be understood that the first portion 36 may be any appropriate shape. Simply, the shape and cross-section of the first portion 36 must interact with the stem bore 30 to allow the rotatable PS post 14 to rotate after implantation. Therefore, other appropriate shapes, such as cylinders, octagons and the like can all be used to define the first portion 36 of the rotatable post. It will be further understood that the second portion 38 of the rotatable post 14 may also define any appropriate shape or cross-section. For example, the second portion 38 of the rotatable post 14 may define a rectangle, square, teardrop, polygon, or any appropriate shape which will allow a selected rotation of the rotatable post 14. Various shapes are described further herein and the interactions with other portions of the tibial component 10 that allow for a selected rotation of the rotatable PS post 14. Similarly, the cross-sectional shapes of the washer 16 or the bearing 18 may be any appropriate selected shape to interact with the second portion 38 of the rotatable post 14 to allow for only a selected rotation of the rotatable post 14.

Figure 3:
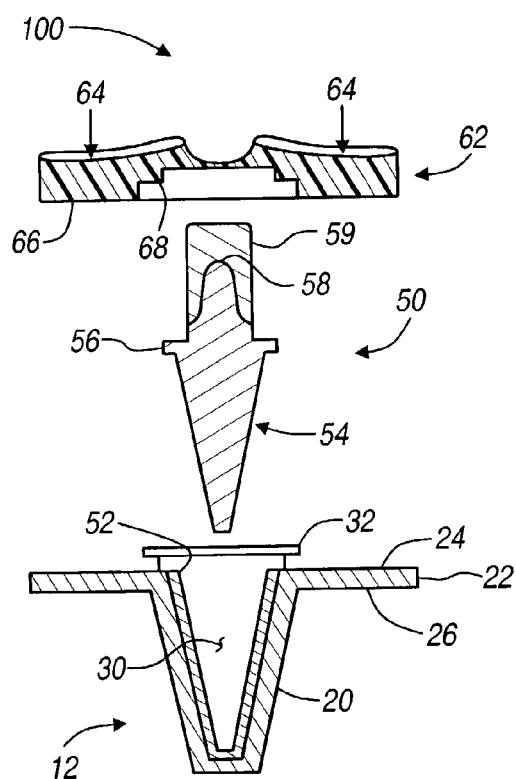
FIG. 3 is an exploded cross-sectional view of a tibial component according to a second embodiment.

With reference to FIG. 3, an alternative embodiment of a tibial prosthetic 100 (where like numerals call-out similar features and portions as illustrated in FIGS. 1 and 2) the tibial prosthetic 100 includes the tibial portion 12. The tibial portion 12 includes the tibial stem 20 that extends into a tibia during implantation. Extending from the tibial stem 20 is the tibial tray 22 that includes the superior portion 24 and the inferior portion 26. As described above, any surface of the tibial portion 12 may be polished or smoothed depending upon the desired friction, bone ingrowth, or lack of friction between different components or bony portions. Formed in the tibial stem 20 is the stem bore 30.

The stem bore 30 can operate with a rotatable PS post 50. Placed or formed within the stem bore 30 is a liner or bushing 52. The post bore liner or bushing 52 can be formed of any appropriate material, such as an UHMWPE. The bushing 52 provides a bearing or liner between the mobile PS post 50 and the tibial portion 12. It will be understood, however, that the liner 52 is not necessary for operation of the tibial prosthetic 100. Rather the post bore lining 52 provides an option to the implanting surgeon, depending upon the patient's particular needs.

The mobile PS post 50 includes an inferior taper or first portion 54 that is adapted to be received within the stem bore 30. Extending from the first portion 54 is a collar or tang 56. Extending superiorly from the tang 56 is a core portion 58. The mobile PS post 50 is formed of a biocompatible metal, such as titanium or alloys of cobalt-chromium molybdenum.

The first portion 54 is received within the stem bore 30 during implantation. Within the stem bore 30, the mobile PS post 50 is able to at least rotate, and may also distract if selected. The first portion 54 of the mobile PS post 50 may be any appropriate shape, such as conical or cylindrical. The stem bore 30 and the post bore bushing 52 define complimentary shapes to receive the first portion 54 of the mobile PS post 50. It will be understood that the complimentary shapes do not lock the mobile PS post 50 in any position, but do allow the mobile PS post 50 to rotate and distract as selected.

The post bore liner 52 provides a bushing between the metal of the mobile PS post 50 and the metal of the tibial portion 12. This allows a smoother rotation of the mobile PS post 50 if the first portion 54 and the anterior of the stem bore 30 are not finished to a fine polished surface. Alternatively, if the liner 52 is not used, the first portion 54 of the mobile PS post 50 can be highly polished as well as the interior of the stem bore 30 to allow for a substantially smooth articulation of the mobile PS post 50 within the stem bore 30.

Molded over the superior metal portion of the core portion 58 is a second portion or superior PS post 59. The second portion 59 forms the constraining portion of the mobile PS post 50, where the second portion 59 operably engages the femur or the femoral implant. Therefore, although the first portion 54 that articulates with the tibial portion 12 is formed of a metal, the second portion 59 of the mobile PS post 50 is formed of a polymer material. Exemplary polymer materials include ultra high molecular weight polyethylenes. This allows for a poly interaction between the mobile PS post 50 and the femoral component. Nevertheless, this composite mobile PS post 50, including a metal first portion 54 and the polymer second portion 70 provides substantial strength to the mobile PS post 50 for the life of the implant.

Extending from the superior side 24 of the tibial tray 22 is a locking portion 32. The locking portion 32 operably engages a portion of a bearing 62. The bearing 62 includes a superior surface which defines condyle, grooves, or bearing surfaces 64 to operably engage the condyles of the femur or femoral implants after implantation of the knee prosthetic. An inferior surface of the bearing 62 includes a tray engaging surface 66 that rests upon the superior portion 24 of the tibial tray 22 after implantation. The inferior surface of the bearing 62 also defines a first ledge 68 that engages the tang 56 of the mobile PS post 50 after implantation. This restricts distraction of the mobile PS post 50 while the mobile PS post 50 remains able to rotate. The shoulder 68, of the bearing 62, may be designed to provide for a selected distraction of the mobile PS post 50 from the stem bore 30.

For example, if it is selected that the rotating PS post 50 will not distract from the stem bore 30, the shoulder 68 can be selected such that it substantially engages the tang 56 of the rotating PS post 50. In this case, the rotating PS post 50 may not distract from the stem bore 30 during use. However, the rotating PS post 50 remains able to rotate while the metal portion of the tang 56 engages the bearing 62 to allow rotation of the rotating PS post 50. Alternatively, the shoulder 68 may be formed so that when it is assembled with the tibial component 12, there is a space between the tang 56 and the shoulder 68. In this case, the rotating post 50 is able to distract from the stem bore 30 in a superior direction. In this situation, the rotating PS post 50 is able to both rotate and distract after implantation. Nevertheless, the mobile PS post 50 may still articulate within the stem bore 30 after implantation.

Figure 4A:
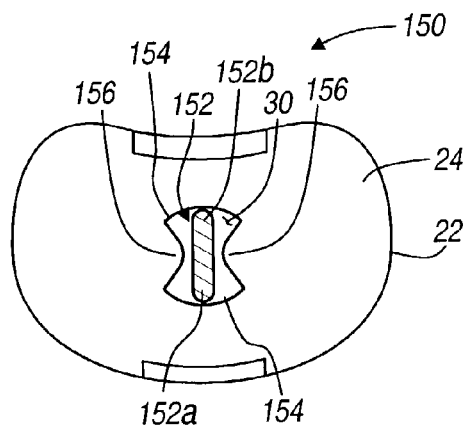
FIGS. 4A–4C is a plan view of a tibial component including a stem bore according a first exemplary embodiment.
Figure 4B:
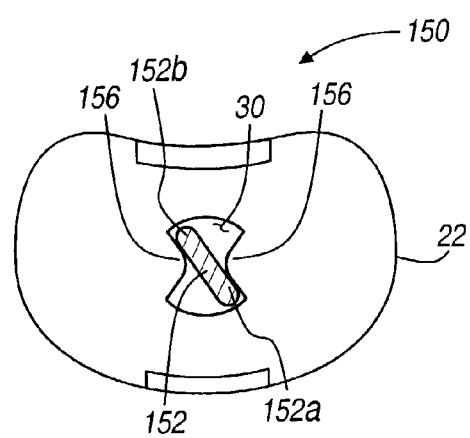
Figure 4C:
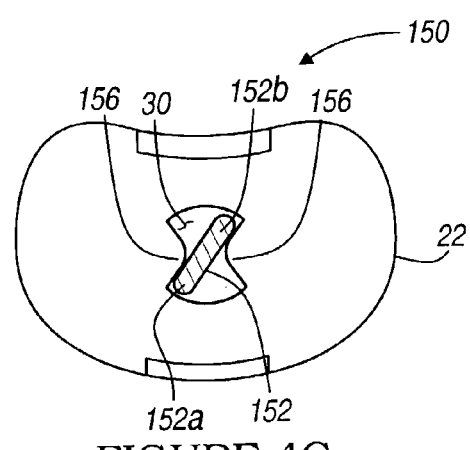

With reference to FIGS. 4A–4C and starting particularly with FIG. 4a, a method of providing a tibial prosthetic 150 to limit the rotation of a rotatable PS post 152 is illustrated and described. Generally, the tibial prosthetic includes a tibial tray 22 having a superior portion 24. Formed substantially in the center of the tibial tray 22 and further defined by the tibial stem (not specifically shown) is the stem bore 30. The bore 30 is formed to receive the first portion of the rotatable post 152. The first portion of the rotatable post 152 may include any particular cross-section to limit the rotation of the rotatable post 152. According to this embodiment, the rotatable post 152 includes a first posterior portion 152a and a second anterior portion 152b. The posterior portion 152a and the anterior portion 152b are spaced apart along a central axis such that the cross-section of the first portion of the rotatable post 152 is substantially elongated. The stem bore 30 defines a shape which compliments the cross-sectional shape of the rotatable post 152 to limit the rotation of the rotatable post 152 to a selected amount. For example, as illustrated here, the stem bore 30 may include generally symmetrical arc regions 154 placed near the anterior and posterior portions of the tibial tray 22. Generally symmetrical triangle regions 156 are placed between the arc regions 154 and generally on the medial and lateral sides of the tibial tray 22.

With continuing reference to FIGS. 4A–4C, the mobile PS post 152 is able to articulate until a portion of it contacts one of the triangle portions 156 of the bore 30. With particular reference to FIG. 4B, the anterior portion 152b of the PS post 152 may rotate laterally, if the implant 150 were placed in a left knee, until the anterior portion 152b contacts one of the edges of the triangular region 156. Similarly, the posterior portion 152a will also reach an edge of the triangular portion 156. It will be understood that the position of the mobile PS post 152 would be medially rotated if the tibial portion was placed in the right knee. Generally, rotation may be allowed to any selected degree. Appropriate ranges include about 1° to about 180° of rotation Nevertheless, it may be limited to about 1° to about 30°.

With particular reference to FIG. 4C, the mobile PS post 152 may also rotate medially, if placed in a left knee, until the anterior portion 152b reaches a superior edge of the triangular portion 156. Similarly, the posterior portion 152a of the mobile PS post 152 will engage the posterior portion 156b of a triangled region as well. It will be understood that similar ranges of rotation are possible in this direction as well. It may also be selected to include different rotational amounts for medial or lateral rotation.

It will be understood that various designs of the bore 30 may be used to select various amounts of rotation of the rotatable PS post 152. Similarly, various designs of the mobile PS post 152 may be chosen to select desired degrees of rotation relative to the bore 30. For example, with reference to FIG. 5, a tibial component 160, including a tibial tray 22 includes a bore 30 to receive a first portion of a mobile PS post 162. The bore 30 defines a substantially "tear drop" cross section. The bore 30 includes an anterior arch 164 that defines a smaller radius than a radius of a posterior arch 166. The mobile PS post 162 includes a complimentary tear drop shape, where an anterior edge 162a has a smaller radius than a posterior edge 162b. However, the size of the perimeter of the mobile PS post 162 is smaller than the interior perimeter of the bore 30, such that the mobile PS post 162 is able to articulate within the bore 30. The area of articulation is substantially at the posterior side of the mobile PS post 162. Substantially, the anterior portion 162 of the mobile PS post 162 defines a pivot point about which the mobile PS post 162 may rotate. Therefore, the posterior portion 162b is able to move medial-laterally within the bore 30 in the direction of arrow A.

Figure 5:
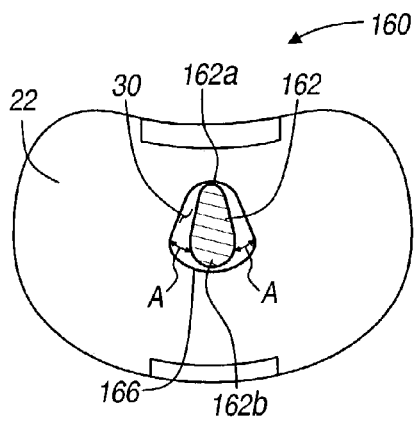
FIG. 5 is a plan view of a tibial component including a stem bore according a second exemplary embodiment.
Figure 5A:
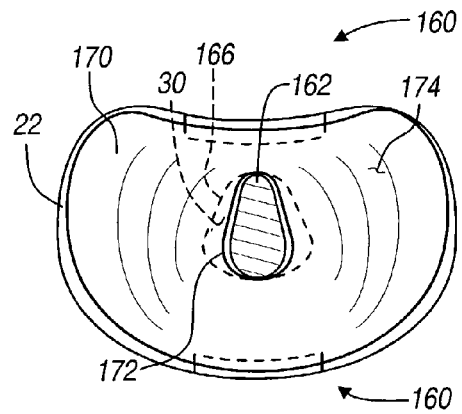
FIG. 5A is a plan view of the device in FIG. 5 including a bearing.

With reference to FIGS. 5 and 5A, a bearing component 170 is placed on the tibial tray 22. The bearing component 170 is locked to the tibial tray using the above-described locking mechanisms. The bearing component 170 defines a mobile or rotatable PS stem bore 172 which is substantially placed over the bore 30 in the tibial stem 20. Nevertheless, the bearing mobile PS stem bore 172 may have different dimensions than the dimensions 166 defining the rotatable PS stem bore 30. A plurality of bearings may be provided which have rotating PS stem bores 172 of variable dimensions. Therefore, although a single dimension of a bore 166 may be defined by the tibial tray 22, a plurality of bore sizes may be defined by the bearing 170. In this way, a physician can determine at the time of the surgery the final rotational allowances provided to the rotatable PS post 14.

Figure 6:
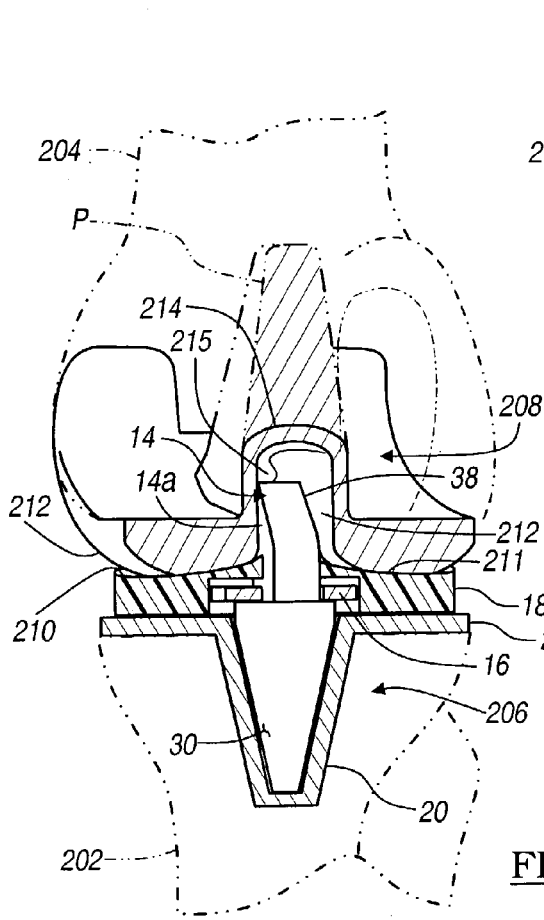
FIG. 6 is an anterior plan view of a knee prosthetic implanted in a knee joint including a femur rotated relative to a tibia.
Figure 6A:
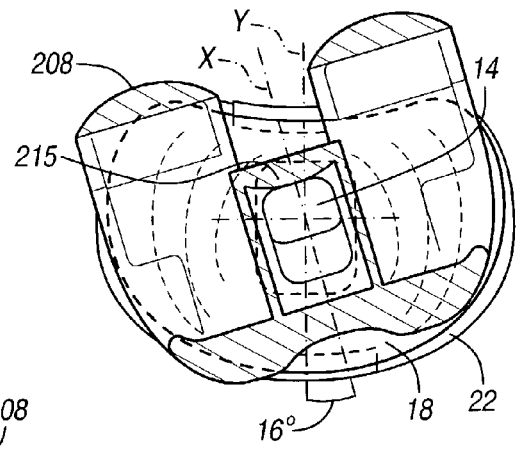
FIG. 6A is a superior plan view of a knee prosthetic rotated.

Moreover, the bearing component 170 may include depressions or articulation areas 174 that substantially allow condyles of a femoral component 208 to articulate therewith (as illustrated in FIG. 6A). The articulation areas 174 are designed in the bearing component 170 to allow ease of rotation of the femoral component 208 relative to the tibial tray 22. Therefore, as the femoral component 208 rotates, it does not ride up on the bearing 170, but rather articulates in the articulation area 174 for ease of rotation.

With reference to FIG. 6, a knee prosthetic 200 can be implanted in the knee joint using any generally known methods. Generally, to implant a knee prosthetic, the knee joint is resected. Specifically, a superior portion of a tibia 202 is resected and an inferior portion of a femur 204 is also resected to receive the various components. A tibial component 206 is implanted on the tibia 202, while the femoral component 208 is implanted on the femur 204.

The tibial component 206 includes a tibial stem 20 and a tibial tray 22. The tibial stem 20 defines a tibial bore 30 that allows the mobile PS post 14 to articulate within the bore 30. The mobile PS post 14 is formed of a polymer material, such that it easily glides within the bore 30. The washer 16 provides for a substantially friction free articulation of the mobile PS post 14 and the bearing 18. The bearing 18 includes a first and second condylar surfaces 210 to receive a first and second condyle 212 of the femoral implant 208. The condyles 212 of the femoral implant 208 allow the femur 204 to articulate in a substantially natural manner relative to the tibial component 206.

Formed between the two condyles 212 is an inter-condylar area or box 214. Although illustrated as a closed box, the inter-condylar area 214 may be defined by only medial and lateral walls. Moreover, the inter-condylar box 214 may define a cam 215 that operably engages the rotating PS post 14. Illustrated in phantom is a post P that may extend from the femoral component 208 to define a constrained femoral component. It will be understood that any appropriate femoral component may be chosen for the particular patient.

The inter-condylar box 214, or the cam 215, operably articulates with the mobile PS post 14. Specifically, the inter-condylar box 214 articulates with the superior portion 38 of the mobile PS post 14. This allows a constraining of the femur 204 relative to the tibia 202 after implantation of the knee prosthetic 200. Simply, the mobile PS post 14 does not allow the femur 214 to translate posteriorly relative to the tibia 202. The mobile PS post 14 is able to rotate medial-laterally within the stem bore 30. As illustrated here, the femur is rotated between about one and about 90 degrees relative to the tibia 202. For illustration only a center axis X of the femoral component 208 is rotated 16 degrees from a center axis Y of the tibial tray 22. The mobile PS post 14 is rotated, with the femur 204 relative to the tibia 202, such that an anterior side 14a of the mobile PS post 14 is substantially aligned with the center line of the femur 204 and angled relative to a center line of the tibia 202.

The femur is able to rotate both medial and laterally relative to the tibia 202. Because the mobile PS post 14 is able to rotate within the stem bore 30, the mobile PS post 14 can be shaped more complimentarily with the inter-condylar box 214 and rotate with the femur 204. Also, the mobile PS post 14 may distract or move proximally from the stem bore 30 if desired. The bearing 18 includes the ledge that engages the washer 16 to keep the mobile PS post 14 substantially within the stem bore 30. However, a selected distraction may be allowed.

Figure 7:
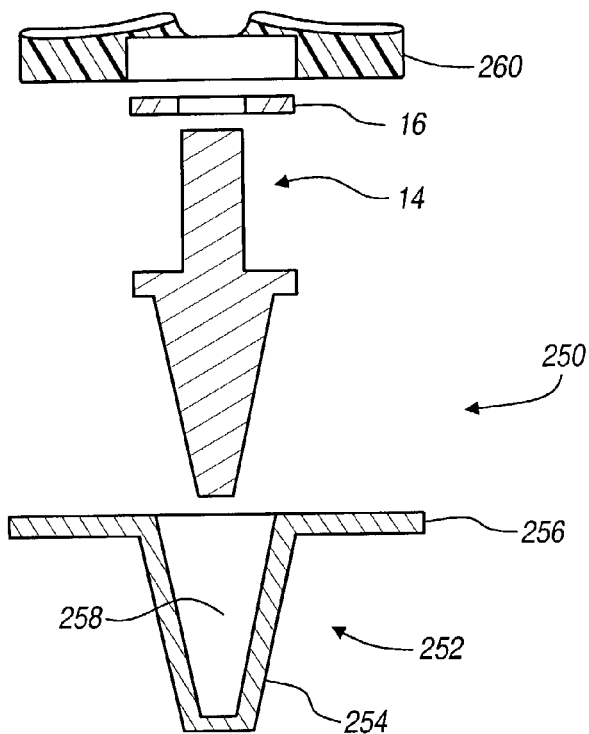
FIG. 7 is an exploded cross-sectional view of a tibial portion including a mobile PS post according to a third embodiment.

With reference to FIG. 7, a tibial prosthetic 250, for implant into a tibia, generally includes a tibial component 252. The tibial component 252 includes a tibial stem 254 and a tibial tray 256. Formed within the tibial stem 254 is a stem bore 258 that allows the rotating PS post 14 to articulate after implantation. A washer 16 allows substantially friction free articulation between a bearing 260 and the mobile PS post 14. Specifically, the mobile post 14 and the bearing 260 may be formed of a polymer material, such as UHMWPE. Contrary to this, the washer 16 is formed of a suitable biocompatible metal and allows for a substantially free motion of the mobile PS post 14 relative to the bearing 260.

The bearing 260 is a mobile bearing and able to articulate relative to the tibial component 252. Therefore, the mobile bearing 260 is able to articulate anterior and posterior after implantation in conjunction with the mobile PS post 14 that is able to rotate after implantation.

Figure 8:
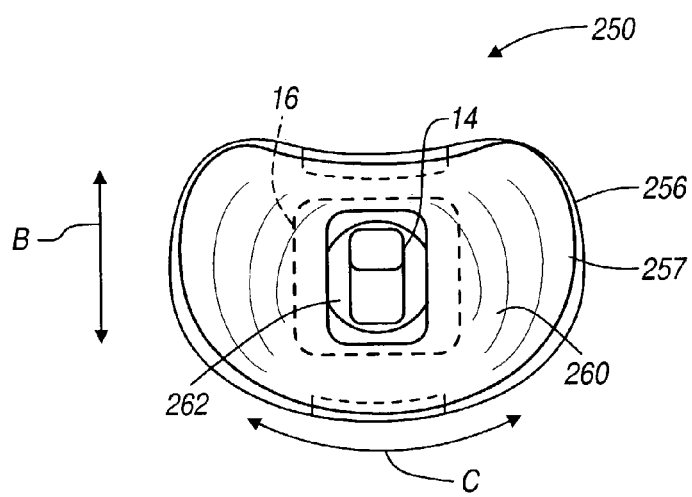
FIG. 8 is an anterior plan view of the knee prosthetic illustrated in FIG. 7.

With continuing reference to FIG. 7 and additional reference to FIG. 8, after implantation the mobile bearing 260 substantially rests on the tibial tray 256. The superior portion of the tibial tray 257 may be highly polished to allow substantially free articulation of a mobile bearing 260 on the tibial tray 256. A region of the mobile bearing 260, substantially near the center of a mobile bearing 260 defines a stem bore or opening 262. The mobile bearing opening 262 allows the mobile bearing 260 to articulate anteriorly and posteriorly without immediately engaging the mobile PS post 14. Therefore, there is a space or open region defined between the mobile PS post 14 and the edges of the bearing opening 262, such that the mobile bearing 260 is able to articulate medial/laterally in the direction of arrow B. Similarly, the mobile bearing 260 is able to rotate medial/laterally in the direction of arc C in conjunction with the mobile PS post 14. Therefore, both the mobile bearing 260 and the mobile PS post 14 are able to articulate with the femur relative to the tibia after implantation. It will be understood, therefore, that the mobile PS post 14 may move independent the bearing 252, and vice-versa. The PS post 14 need not move in tandem with the mobile bearing 252.

Figure 9:
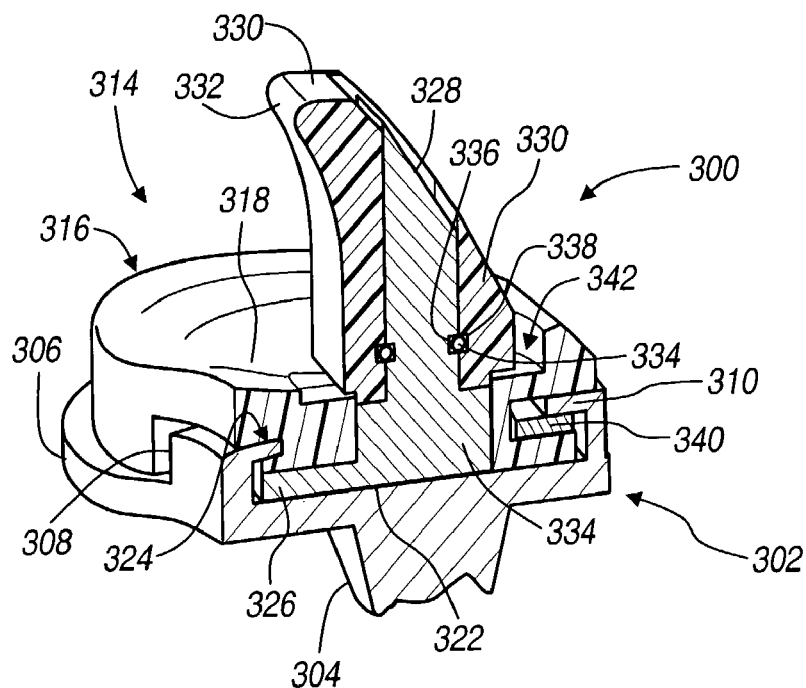
FIG. 9 is an exploded, partial cross-sectional view of a fixed bearing and rotating post according to an embodiment.
Figure 10:
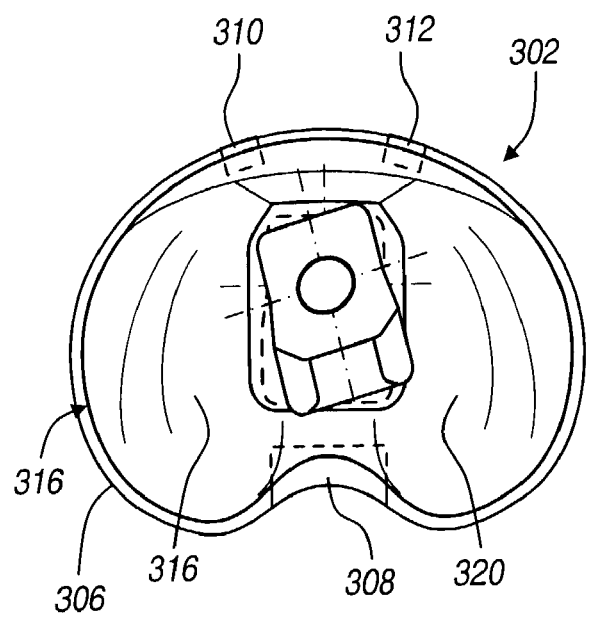
FIG. 10 is a cross-sectional view of the implant in FIG. 9 fully assembled.

With reference to FIGS. 9 and 10, a tibial component 300 is illustrated. The tibial component generally includes a tibial implant 302 which is adapted to be implanted into a tibia. The tibial component 300 includes a tibial stem 304 and a tibial tray 306 extending therefrom. The tibial tray 306 is provided to cover a substantial portion of a superior end of the tibia after it has been resected. Extending from the tibial tray 306 are a plurality of locking portions including a posterior locking portion 308 and anterior locking portions 310 and 312. The superior portion of the tibial tray 306 may be polished or provided an appropriate finish.

A bearing and stem portion 314 is provided which may interlock with the tibial portion 302. The bearing portion 314 includes a bearing member 316 that has a first condyle surface 318 and a second condyle surface 320. Operably connected to the bearing member 316 is a first or metal portion 322. The metal portion 322 may be molded or adhered, or otherwise affixed, to the bearing portion 316. The bearing portion 316 is generally made of polymer such as UMHWPE. The metal portion 322 is generally immobile relative the bearing member 316.

In addition, the bearing member 316 defines a first or posterior locking section 324. The posterior locking portion 324 engages the locking member 308 that extends from the tibial portion 302. This assists in holding the bearing portion 314 relative the tibial portion 302. Similarly, a locking tang or finger 326 extends posteriorly from the metal portion 322 to also engage the locking member 308. This holds the metal portion 322 fixed relative the tibial portion 302. The tang 326 further assists in holding the bearing member 316 relative the tibial portion 302.

The metal portion 322 defines a metal or core post 328 which extends superiorly from the bearing member 316. A post cap or second portion 330 is then positioned over the post 328 extending superiorly from the metal portion 322. The post cap 330 is generally formed of a polymer, such as UHMWPE. The post cap 330 defines a rotatable PS post.

The post cap 330 is allowed to rotate relative the metal post 322. Therefore, although the metal portion 322 and the metal post 328 are fixed relative the tibial portion 302, the post cap 330 can rotate relative the tibial portion 302. Moreover, the poly cap 330 may be selected in any appropriate shape. For example, a posterior hook 332 may be selected to be defined by the post cap 330. This assists engaging the femur or femoral component after implantation.

The post cap 330 may engage the metal post 328 in any appropriate manner. For example, a locking ring 334 may operably interconnect the post cap 330 and the metal post 328 through a post groove 336 and a cap groove 338. The locking ring allows the post cap 330 to be slipped over the metal post 328 and held in place. However, although the post cap 330 is not able to substantially distract once locked in place with the ring 334, the post cap 330 can rotate relative the metal post 328. Alternatively, a screw or other locking portion may be threaded into the metal post 328 after the post cap 330 is placed thereon to hold the post cap 330 in place.

The bearing portion 316 also defines an interior locking area 340. Moreover, the superior portion of the bearing member 316 defines a post groove 342. The post groove 342 allows an area for the post cap 330 to rotate and not bind the post cap 330 with the bearing member 316. However, the post groove 342 can include a selected geometry such that only a selected amount of rotation is allowed to the post cap 330.

It will also be understood that the mobile PS post, as illustrated in any of the above described exemplary embodiments, may be used in conjunction with a more constrained knee. Specifically, each of the knees illustrated in the figures and described above are posterior stabilized knee prosthetics where the mobile PS post provides a posterior stabilization of the knee after implantation. Alternative knees, include substantial constraints, such as hinges and other inflexible portions, which provide for a higher constraint of the knee after implantation. Therefore, more constraint is provided in various knees, but the mobile PS post can be used with these knees to provide for a more desirable knee configuration.

It will be understood that each of the exemplary and alternative embodiments may be used in conjunction with one another. For example, an all-poly mobile PS post, such as the mobile PS post 14 illustrated in FIG. 1, can include any appropriate shape to limit or allow as much or as little desired rotation. For example, the all-poly post may be formed in a substantially tear-drop shape to operably interact with a tear-drop bore in the tibial component to limit the range of rotational motion. Similarly, the metal and poly mobile PS post 50, as illustrated in FIG. 3, may be substantially elongated posteriorly to anteriorly to engage various portions of a bore to limit rotational motion of the mobile PS post 50. Therefore, the various illustrated embodiments described herein are not to limit the appended claims, but merely provide examples of configurations of knee and tibial components concluding a mobile PS post.

A knee prepared to receive the knee prosthetic as described herein can be prepared using generally known means. For example, the tibia can be resected to provide a tibial plateau and be reamed to provide an area to receive the tibial stem as described above. However, various other methods can also be used to implant the presently described prosthetic. For example, during implantation a decision can select the amount of rotation desired for the rotating PS post. For example, and with reference to FIG. 5 above, the length or dimension of the posterior side 162b of the mobile PS post 162 can be selected to determine the amount of motion allowed in the direction of arrows A. For example, a greater dimension of the posterior side 162b will allow for less rotation of the rotating PS post 162. Contrary, a smaller size of the posterior side 162b will allow for greater rotation of the rotating post 162. Therefore, during the implant procedure, a physician can determine the amount of rotation that is best for a particular patient, depending upon the patient's needs or desires, and implant the rotating PS post 162 that has the appropriate dimensions to allow the selected amount of rotation.

Moreover, the particular type of rotating PS post desired can also be selected. That is, the physician can determine whether an all poly rotating PS post 14, modular or composite rotating PS post 50, or a combined bearing and rotating PS post and a bearing 314 is most applicable to a particular patient or situation. Therefore, a physician can determine intra-operatively the particular components to be implanted in the knee prosthetic.

Although the above description illustrates providing a rotatable PS post as a constraining member, according to various embodiments, it will be understood that various other constraining portion or members may be added to the prosthetic knee. For example, and as illustrated above particularly in FIG. 6, a constrained femoral component including a post P may also be used in conjunction with the various embodiments of the rotatable PS post. In addition, it will be understood that other components interconnecting the tibial component and the femoral component, according to the various embodiments, may also be provided. For example, an artificial tendon can be used to interconnect the femoral component and the tibial component to enhance or provide rollback of the femoral component relative the tibial component such as described in commonly assigned U.S. patent application Ser. No. 10/082,514, filed Feb. 25, 2002, entitled "Method and Apparatus for Mechanically Reconstructing Ligaments in a Knee Prosthesis." Therefore, providing only one constraining member, such as the rotatable PS post, is not necessary and is only an exemplary embodiment.

This description is merely exemplary in nature and, thus, variations that do not depart from the gist are intended to be within the scope of the following claims. Such variations are not to be regarded as a departure from the spirit and scope.

What is claimed is:

1. A knee joint prosthesis for implantation to replace a portion of a knee joint, comprising:
    a tibial component including a tibial tray;
    a bearing member operable to engage said tibial tray, wherein said bearing member is fixed relative to said tibial tray; and
    a post extending outwardly from said tibial tray and past said bearing member;
    wherein said post is able to move a selected amount restricted at least in part by said bearing member after implantation of the prosthesis.

2. The prosthesis of claim 1, further comprising:
    a femoral component including a first condyle, a second condyle, and an inter-condylar articulation region;
    wherein said bearing member includes a first bearing surface and a second bearing surface to articulate with said first condyle and second condyle, respectively.

3. The prosthesis of claim 2, wherein said post includes a second portion that operably engages said inter-condylar articulation region to constrain said femoral component.

4. The prosthesis of claim 2, wherein said intercondylar articulation region includes a cam.

5. The prosthesis of claim 2, wherein said femoral component is selected from a group consisting of cruciate retaining, posterior stabilized, fully constrained, and hinged.

6. The prosthesis of claim 1,
wherein said post includes a first portion and a second portion;
wherein said first portion defines a selected shape to substantially limit a motion of said post to a selected amount.

7. The prosthetic of claim 1, wherein said post includes a posterior stabilizing post to limit at least one of a posterior motion and an anterior motion of said femoral component.

8. A knee joint prosthesis for implantation to replace a portion of a knee joint, comprising:
a tibial component including a tibial tray;
a bearing member operable to engage said tibial tray, wherein said bearing member is fixed relative to said tibial tray; and
a post extending superiorly from said tibial tray and past said bearing member;
wherein a cap positioned relative to said post is able to move a selected amount restricted at least in part by said bearing member after implantation of the prosthesis.

9. The prosthesis of claim 8, further comprising:
a femoral component including a first condyle, a second condyle, and an inter-condylar articulation region;
wherein said bearing member includes a first bearing surface and a second bearing surface to articulate with said first condyle and second condyle, respectively.

10. The prosthesis of claim 9, wherein said post includes a second portion that operably engages said inter-condylar articulation region to constrain said femoral component.

11. The prosthesis of claim 9, wherein said intercondylar articulation region includes a cam.

12. The prosthesis of claim 9, wherein said femoral component is selected from a group consisting of cruciate retaining, posterior stabilized, fully constrained, and hinged.

13. The prosthesis of claim 8,
wherein said post includes a first portion and a second portion;
wherein said first portion defines a selected shape to substantially limit a motion of said post to a selected amount.

14. The prosthetic of claim 8, wherein said post includes a posterior stabilizing post to limit at least one of a posterior motion and an anterior motion of said femoral component.

15. A knee joint prosthesis for implantation to replace a portion of a knee joint, comprising:
a tibial component including a tibial tray;
a bearing member operable to engage said tibial tray, wherein said bearing member is fixed relative to said tibial tray; and
a post extending outwardly from said tibial tray and through said bearing member;
wherein a cap positioned relative to said post is able to move a selected amount restricted at least in part by said bearing member after implantation of the prosthesis.

* * * * *